United States Patent [19]

Morgan et al.

[11] Patent Number: 5,354,858

[45] Date of Patent: Oct. 11, 1994

[54] PRODUCTION AND USE OF DIELS ALDER ADDUCTS OF VINYL PORPHYRINS AND OF COMPOSITIONS CONTAINING SUCH ADDUCTS

[75] Inventors: Alan R. Morgan, Swanton; Steven H. Selman, Toledo, both of Ohio

[73] Assignees: The University of Toledo; Medical College of Ohio, both of Toledo, Ohio

[21] Appl. No.: 912,079

[22] Filed: Jul. 8, 1992

Related U.S. Application Data

[63] Continuation of Ser. No. 677,408, Mar. 28, 1991, abandoned.

[51] Int. Cl.$^5$ .......................................... C07D 487/22
[52] U.S. Cl. ................................................... 540/145
[58] Field of Search ................. 540/145; 514/185.397, 514/410; 534/13, 14, 16

[56] References Cited

U.S. PATENT DOCUMENTS

| | | | |
|---|---|---|---|
| 4,883,790 | 11/1989 | Levy et al. | 540/145 |
| 4,908,442 | 3/1990 | Narang et al. | 540/145 |
| 4,996,312 | 2/1991 | Sakata et al. | 540/145 |

OTHER PUBLICATIONS

Yan–Hu et al, Tetrahedron Letters vol. 30(45) pp. 6135–6138, 1989.

Morgan et al, "Diels–Alder Adducts of Vinyl Porphyrins," Journal of Medicinal Chemistry, 33, p. 1258 et seq, 1990.

Chang et al, "A Novel Method of Functionalizing the Ethyl Chain of Octaethylposphyrin", J. Org. Chem. 52, pp. 926–929, 1987.

Selman et al, "Blood Flow in Transplantable Bladder Tumors Treated with Hematoporphycis Derivative and Light, Cancer Research", pp. 1924–1927, May 1984.

Pangka et al, "Diels–Alder Reactions of Protoporphyrin IX Dimethyl Ester with Electron–Deficient Alkynes", J. Org. Chem, 51, 1094–1100, 1986.

Morgan et al, "Ready Syntheses of Benzoporphyrins Via Diels–Alder Reactions with Protoporphyrin IX", J. Chem. Soc. Chem Common., pp. 1047–1048, 1984.

David Dolphin, The Porphyrins, vol. 1, Structure & Synthesis, Part A., pp. 85–234, 1978.

*Primary Examiner*—John M. Ford
*Attorney, Agent, or Firm*—John C. Purdue; David C. Purdue

[57] ABSTRACT

Families of Diels Alder adducts and of metal complexes of Diels Alder adducts, which are useful as particularly active compounds for use in photodynamic therapy, are disclosed. The Diels Alder adducts and a preferred family of metal complexes have the structures of Formula 1, Formula 2, Formula 3 and Formula 4, below:

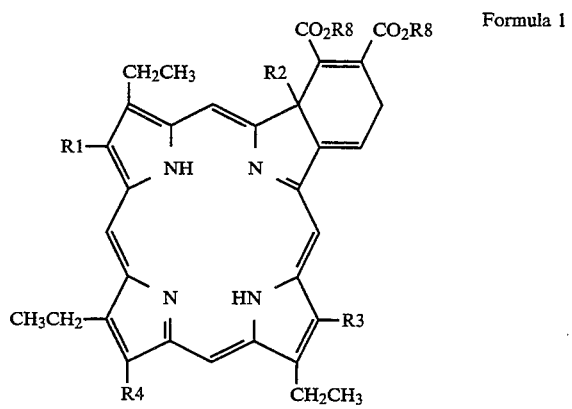

Formula 1

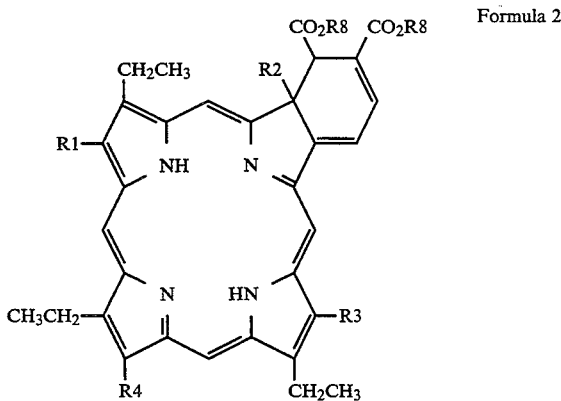

Formula 2

(Abstract continued on next page.)

ABSTRACT -continued

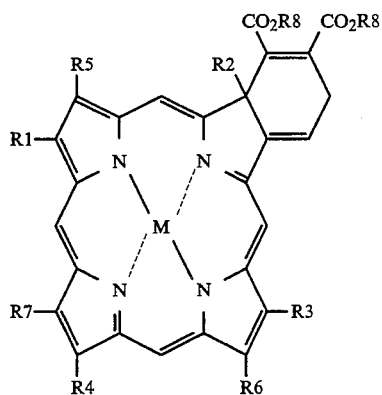

Formula 3

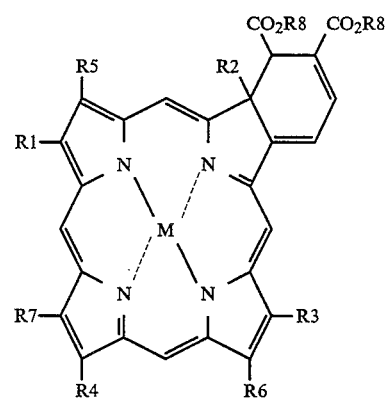

Formula 4 where R1, R2, R3 and R4 can be the same or different, and each is methyl or ethyl, R5, R6 and R7 are ethyl, R8 is an alkyl group other than t-butyl having from one to four carbon atoms and M comprises a metal cation, e.g., Sn or Zn, that is complexed with two of the nitrogens of the adduct. The use of the adducts and complexes in photodynamic therapy is also disclosed.

3 Claims, No Drawings

PRODUCTION AND USE OF DIELS ALDER ADDUCTS OF VINYL PORPHYRINS AND OF COMPOSITIONS CONTAINING SUCH ADDUCTS

STATEMENT AS TO RIGHTS TO INVENTIONS MADE UNDER FEDERALLY-SPONSORED RESEARCH AND DEVELOPMENT

This invention was made with Government support under Grant RO1CA43006 by the National Institutes of Health. The Government has certain rights in the invention.

REFERENCE TO RELATED APPLICATION

This is a continuation of application Ser. No. 07/677,408, filed Mar. 28, 1991, now abandoned.

FIELD OF THE INVENTION

This invention relates to the production and use of new Diels Alder adducts of vinyl porphyrins, to the production and use of metal complexes of these and other adducts, to the production and use of compositions containing such adducts and metal complexes, and to a method for detecting and treating tumors which involves administering a Diels Alder adduct or metal complex and, after a suitable period of time, irradiating the tumor or suspected tumor with visible or ultra violet light of a suitable wavelength. Specifically, the new Diels Alder adducts, which are useful as particularly active compounds for use in photodynamic therapy, have the structures of Formula 1 and Formula 2, below:

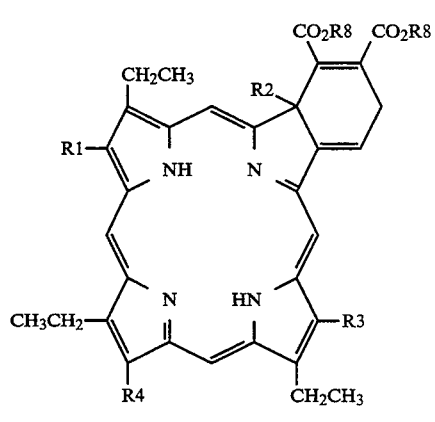

Formula 1

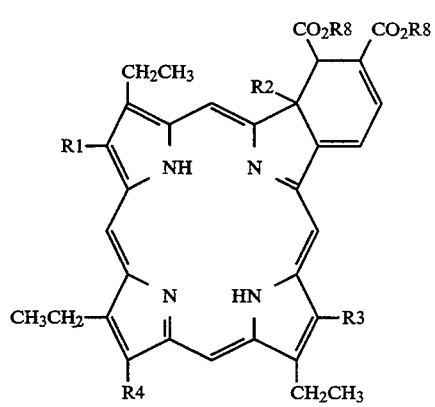

Formula 2 where R1, R2, R3 and R4 can be the same or different, and each is methyl or ethyl, and R8 is an alkyl group other than t-butyl having from one to four carbon atoms. The new metal complexes of the foregoing Diels Alder adducts have the structure of Formula 3, Formula 4, Formula 5, Formula 6, Formula 7 or Formula 8, below:

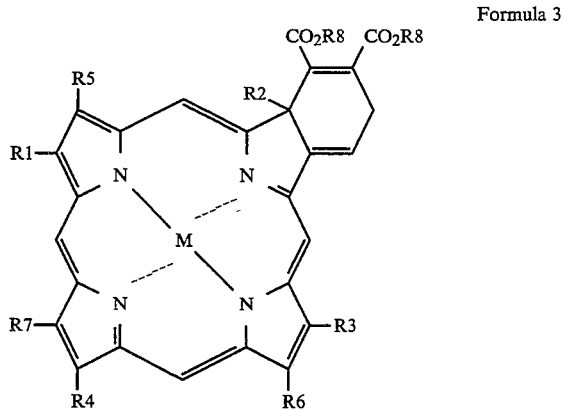

Formula 3

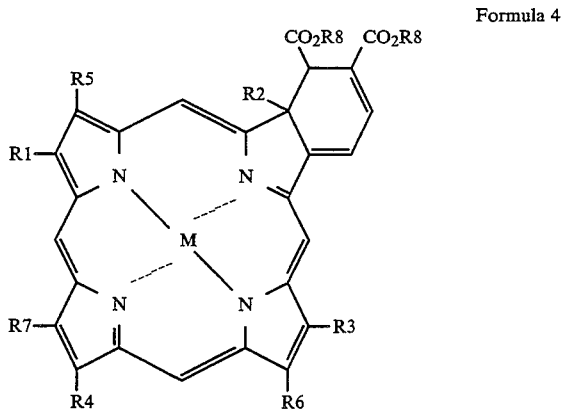

Formula 4

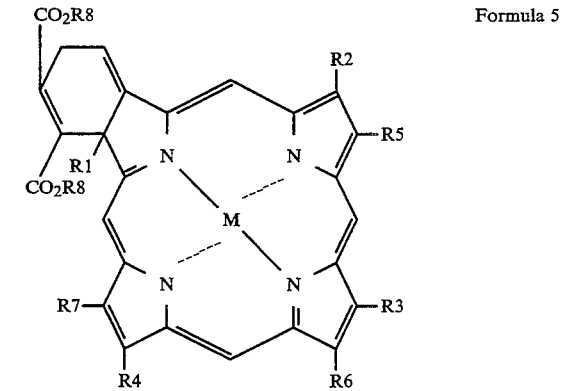

Formula 5

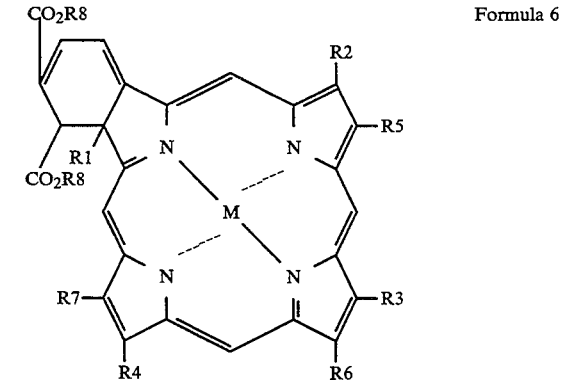

Formula 6

-continued

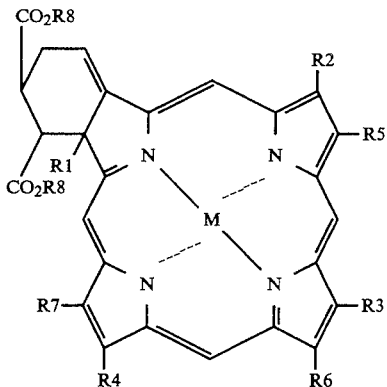

Formula 7

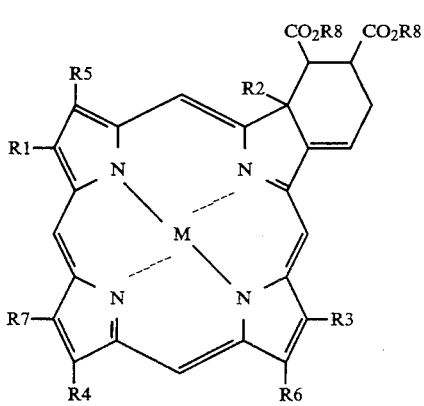

Formula 8 where R1, R2, R3, R4, R5, R6 and R7 can be the same or different, and each is an alkyl group other than t-butyl having from one to four carbon atoms, an alkylene group having from 2 to 4 carbon atoms, a group having the formula $R_2N(R_3)_2$ where $R_2$ is a bivalent aliphatic hydrocarbon radical having from 1 to 4 carbon atoms, wherein any carbon to carbon bond is either a single or a double bond, and not more than one is a double bond; $R_3$ is hydrogen or an alkyl group having from 1 to 2 carbon atoms and the two $R_3$ groups can be the same or different, an amino acid moiety which is a part of an amide produced by reaction between an amine function of a naturally occurring amino acid and a carbonyl function of the adduct, a monoclonal antibody moiety which is attached to the adduct moiety through a carbonyl which is a part of an amide produced by reaction between an amine function of a monoclonal antibody and a $CO_2R'$, $CH_2CO_2R'$ or $CH_2CH_2CO_2R'$ group of the adduct, and wherein the moiety is of a monoclonal antibody which selectively binds to malignant tumors, a group having the formula $R_2N(R_4)_3A$ where $R_2$ is a bivalent aliphatic hydrocarbon radical having from 1 to 4 carbon atoms, wherein any carbon to carbon bond is either a single or a double bond, and not more than one is a double bond; A is a physiologically acceptable anion; and $R_4$ is an alkyl group having from 1 to 2 carbon atoms and the three $R_4$ groups can be the same or different, a group having the formula $R_2OH$ where $R_2$ is a bivalent aliphatic hydrocarbon radical having from 1 to 4 carbon atoms, wherein any carbon to carbon bond is either a single or a double bond, and not more than one is a double bond, an ester having the structure $CO_2R'$, $CH_2CO_2R'$ or $CH_2CH_2CO_2R'$, where R' is hydrogen or an alkyl group other than t-butyl having from 1 to 4 carbon atoms, R8 is an alkyl group other than t-butyl having from one to four carbon atoms, and M comprises a metal cation that is complexed with two of the nitrogens of the adduct and is Ag, Al, Ce, Co, Cr, Dy, Er, Eu, Ga, Gd, Hf, Ho, In, La, Lu, Mn, Mo, Nd, Pb, Pd, Pr, Pt, Rh, Sb, Sc, Sm, Sn, Tb, Tc-99m, Th, Ti, Tl, Tm, U, V, Y, Yb, Zn or Zr.

Formula 1, where R8 is methyl, is reproduced below, with the numbers 1 through 12 added to identify some of the carbon atoms in the Diels-Alder adduct of Formula 1; the same numbering is used herein to identify the corresponding carbon atoms in the Diels-Alder adduct of Formula 2 and in the metal complexes of Formulas 3 through 8 (this is not the conventional numbering used in porphyrin chemistry, where numbers are assigned to all the carbons in the nucleus). The carbons that are numbered in the following formula are those which are capable of being substituted in the parent porphyrin. The R1, R2, R3 and R4 substituents are on the 1, 4, 7 and 10 carbon atoms while the ethyl substituents are on the 2, 8, and 11 carbon atoms, and the six-membered exocyclic ring is fused to the 4 and 5 carbon atoms.

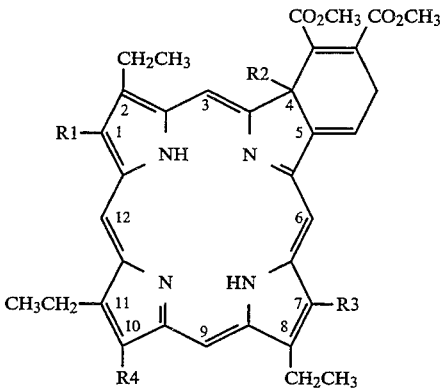

DISCUSSION OF RELATED ART

Various modified porphyrins which appear green because they absorb light in the orange-red range of wavelengths are disclosed in "Levy et al." (U.S. Pat. No. 4,883,790, granted Nov. 28, 1989 for WAVELENGTH-SPECIFIC CYTOTOXIC AGENTS; a "modified porphyrin" is sometimes called a Gp in the patent). Levy et al. also discloses conjugates of the modified porphyrins and of hematoporphyrin ("Hp") with receptor ligands which are capable of binding to cell surfaces and with immunoglobulins or immunologically reactive portions of immunoglobulins. The conjugates can be composed, the patent states, of modified porphyrins or Hp covalently bonded to receptor ligands, immunoglobulins or immunologically reactive immunoglobulin portions or of modified porphyrins covalently bonded to linking moieties which are in turn covalently bonded to the receptor ligands, immunoglobulins or immunologically reactive immunoglobulin portions. The preferred modified porphyrins (and the only ones that are specifically disclosed) are "obtained using Diels-Alder reactions with porphyrin nuclei under conditions which effect a reaction at only one of the two available conjugated, nonaromatic diene structures present in the protoporphyrin-IX nucleus". (column 3, lines 4 and following). Levy et al. also states (column 3, lines 36 et seq.):

"Specific preparation of compounds useful in the invention is described by Morgan, A. R., et al., *J Chem Soc Chem Commun* (1984) pp. 1047–1048; and by Pangha, B. S. et al., *J Organic Chem* (1986) 51:1094. As described in these publications, protoporphyrin-IX dimethyl ester, when reacted with strong Diels-Alder dienophile reagents such as tetracyanoethylene, is derivatized to the dyhydro-dibenzo derivatives. However, when more weakly electron withdrawing groups are utilized on the Diels-Alder reagent, hydromonobenzo derivatives are formed. Thus, there are obtained compounds shown as formulas 1 and 2 of FIG. 1 wherein $R^1$ and $R^2$ represent the original Diels-Alder reagent substituents and $R^3$ represents the substituents natively or originally on the porphyrin nucleus."

Protoporphyrin IX dimethyl ester has the following structure:

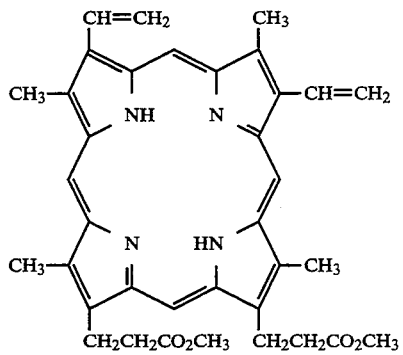

The patent specifically discloses six modified porphyrins (formulas 1-6 of FIG. 1) all of which retain one of the vinyl groups of the protoporphyrin IX dimethyl ester, so that the ethyl substituent on the 2 carbon in the compounds of the instant invention is vinyl in three of the modified porphyrins of the patent. In the other three modified porphyrins, the exocyclic ring is fused to the 1 and 2 carbons and there is a vinyl substituent on the 5 carbon. In all six of the modified porphyrins, there is a methyl substituent on the 11 carbon, where the compounds of the instant invention have an ethyl substituent.

The Levy et al. patent also reports the assessment of the "efficacy of the conjugates and of the Gp compounds of the invention in vivo" (column 11, lines 5 and 6) by tests that are identified, and includes Table 4, which gives test data for Hp, for two Hp conjugates (one with "C-Mab" which is called an "irrelevant monoclonal preparation" and one with "B16G antibody"), for a mixture of B16G antibody and Hp and for two controls: phosphate buffered saline and B16G antibody, stating that similar results "are obtained for Gp alone or Gp conjugates". Table 4 gives, among other data, the percent of animals that were tumor free after 100 days; this percentage ranges from 12.5 to 43 for five of the Hp conjugates tested, and is zero for the Hp conjugate with C-Mab, for all of the compositions which contained Hp or Hp plus B16G antibody, and for the controls. The Levy patent neither discloses nor suggests metal complexes of the Diels Alder adducts with which it is concerned.

BRIEF DESCRIPTION OF THE PRESENT INVENTION

The present invention is a family of Diels-Alder adducts which have the structure of one of Formulas 1 and 2, above, where R1, R2, R3 and R4 can be the same or different, and each is methyl or ethyl. The invention is also a family of metal complexes of Diels Alder adducts having the structure of one of Formulas 3, 4, 5, 6, 7 and 8, above, and a method for detecting and treating tumors which involves the administration of one of the Diels-Alder adducts or metal complexes to a human or animal patient with a tumor, and, after a suitable period of time, irradiation of the tumor with ultraviolet or visible light of a suitable wavelength. The present inventors coauthored with others a paper which was published on Apr. 1, 1990, (*Journal of Medicinal Chemistry*, 33, pages 1258 et seq. [1990]) disclosing, inter alia, the preparation of two Diels-Alder adducts according to the instant invention and their efficacy in the treatment of transplantable FANFT-induced rat bladder tumors.

DESCRIPTION OF THE PREFERRED EMBODIMENTS

The following examples constitute the best modes presently contemplated by the inventors, but are presented solely to illustrate and disclose the invention, and are not intended to be limiting.

As used herein, and in the appended claims, the terms "percent" and "parts" refer to percent and parts by weight, unless otherwise indicated; g means gram or grams; mg means milligram or milligrams; ng means nanogram or nanograms; pg means picogram or picograms; cm means centimeter or centimeters; mm means millimeter or millimeters; L means liter or liters; mL means milliliter or milliliters; μL means microliter or microliters; m/o means mole percent, and equals 100 times the number of moles of the constituent designated in a composition divided by the total number of moles in the composition; v/v means percent by volume; w/v means weight per unit of volume, and is in terms of g/L; M means molar and equals the number of gram moles of a solute in one liter of a solution; μM means micromolar and equals the number of microgram moles in one liter of a solution; mM means millimolar and equals the number of milligram moles of a solute in one liter of a solution; N means normal, and equals the number of gram equivalents of a solute in one liter of solution; and μN means micronormal and equals the number of microgram equivalents of a solute in one liter of solution. All temperatures are in °C., unless otherwise indicated.

Example 1 describes the production of a Diels-Alder adduct ("Adduct I") of 2-vinyl-3,7,8,12,13,17,18-heptaethylporphyrin ("Porphyrin I"; Chang, C. K. et al., *J. Org. Chem.* 52, 926 [1987]) from Porphyrin I and dimethyl acetylenedicarboxylate. Adduct I has the structure of Formula 1 where R1, R2, R3 and R4 are ethyl. Porphyrin I has the following structure, which is a general formula for vinyl porphyrins which can be used to produce Diels Alder adducts according to the invention. In Porphyrin I, R1, R2, R3 and R4 are ethyl:

Vinyl Porphyrins

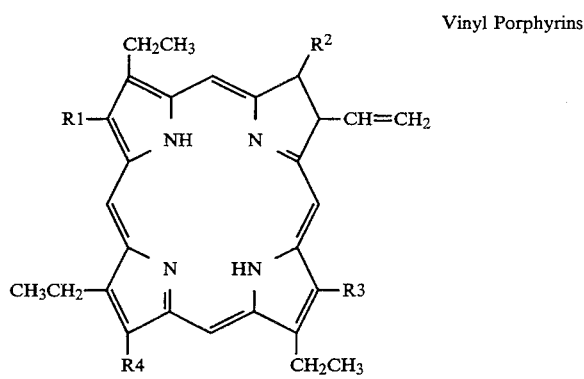

Dihydroxy Chlorins

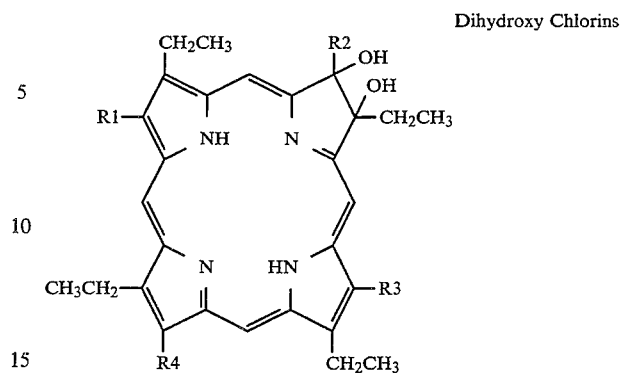

EXAMPLE 1

Adduct I was synthesized from a solution of 20 mg Porphyrin I and 1 mL dimethyl acetylenedicarboxylate in 30 mL toluene. The solution was heated under reflux for about 120 hours until an absorbance band of the Porphyrin I at 624 nm disappeared and an absorbance band appeared at 653 nm. The solution was cooled; the solvent was removed under reduced pressure; and the residue was chromatographed on silica gel using dichloromethane containing 2v/v diethyl ether and 2v/v toluene as the eluent. A red band (first) and a green band (second) were collected. The solvent was removed from the red band under reduced pressure; and the residue was recrystallized from a dichloromethane-methanol solvent, yielding 7 mg Porphyrin I. The solvent was removed from the green band under reduced pressure; and the residue was recrystallized from a dichloromethane-methanol solvent, yielding Adduct I (30 percent of theory), which was identified by $^1$H NMR spectroscopy; $\lambda_{max}$ 651, 594, 534, 499, 400 ($\epsilon$25201, 3046, 5999, 7062, 75951).

Example 2 describes the preparation of 2-vinyl-7,12,17-triethyl-3,8,13,18-tetramethylporphyrin ("Porphyrin II") and the production of a Diels-Alder adduct ("Adduct II") of Porphyrin II and dimethyl acetylenedicarboxylate. Adduct II has the structure of Formula 1 where R1, R2, R3 and R4 are methyl. Porphyrin II has the foregoing general formula for vinyl porphyrins from which Diels Alder adducts according to the invention can be produced. In Porphyrin II, R1, R2, R3 and R4 are methyl. The preparation of Porphyrin II from 2,3-Dihydroxy-2,7,12,17-tetraethyl-3,8,13,18-tetramethylchlorin ("Chlorin I"; Chang et al., *J. Org. Chem.* 1987, 52, 926) is described first. Chlorin I has the following structure, which is general for dihydroxy chlorins from which vinyl porphyrins can be produced; in Chlorin I, R1, R2, R3 and R4 are methyl:

EXAMPLE 2
PREPARATION OF PORPHYRIN II

Porphyrin II was prepared from 25 mg Chlorin I by reaction with phosphorus pentoxide for five hours at 140°. The phosphorus pentoxide and a 25 mL beaker which contained the Chlorin I were placed in a vacuum oven which was maintained at a pressure of 10 mm during the reaction. After the reaction, the solid in the beaker was removed from the oven, and cooled. The soluble portion was then dissolved in the minimum amount of dichloromethane. The mixture which resulted was chromatographed on silica gel, using 60v/v hexane in dichloromethane as the eluent.

PRODUCTION OF ADDUCT II

Adduct II was synthesized from a solution of 20 mg Porphyrin II and 1 mL dimethyl acetylenedicarboxylate in 30 mL toluene. The solution was heated under reflux for about 96 hours until the absorption spectrum indicated that the Porphyrin II had all reacted. Two bands, one of which was identified by NMR spectroscopy as Adduct II, were recovered from the crude product by chromatography.

Example 3 describes the chemical shift of Adduct I to produce Adduct III, a compound having the structure of Formula II where R1, R2, R3 and R4 are ethyl, and the chemical shift of Adduct II to produce Adduct IV, a compound having the structure of Formula II where R1, R2, R3 and R4 are methyl.

EXAMPLE 3

Solutions containing, in one case, 10 mg Adduct I and a few drops of triethanolamine in 10 mL dichloromethane is refluxed for two hours and, in a second case, 10 mg Adduct II and a few drops of triethanolamine in 10 mL dichloromethane are refluxed for two hours. The solvent and excess triethanolamine are then removed in vacuo, and the crude product is purified by chromatography, producing almost quantitative yields of Adduct III and of Adduct IV.

Adduct I and Adduct II were used in in vivo testing conducted on male Fischer CDF(F344)/CrlBr rats weighing 135 to 150 g in whose flanks two transplantable FANFT-induced rat bladder tumors (AY-27) had been grafted subcutaneously. (Use of this system is reported by Selman, S. H., et al., *Cancer Research*, pp. 1924–1927, May, 1984.) When the tumors reached one cm in transverse diameter the animals were injected with sensitizer.

The two adducts were dissolved in a commercially available non-ionic solubilizer and emulsifier obtained by reacting ethylene oxide with castor oil in a ratio of 35 moles of ethylene oxide per mole of castor oil, diluting the resulting solution with 1,2-propanediol, and producing an emulsion with the resulting solution and 0.9 percent aqueous sodium chloride solution. The specific non-ionic solubilizer used is available from BASF under the designation CREMOPHOR EL; it is composed of fatty acid esters of polyglycols, glycerol polyglycols, polyethylene glycols and ethoxylated glycerol. The test solutions were prepared from 50 mg portions of each of the adducts, about 1 mL warm solubilizer (enough to dissolve the test compound), and enough 1,2-propanediol to make a solution of the adduct in a mixed diol/solubilizer solvent containing 32.9 percent solubilizer; finally, enough 0.9 percent aqueous sodium chloride was added to make 10 mL test solution so that the final concentration of the adduct in the test solution was 5 mg per mL. Each test solution was made, with mechanical shaking and stirring, by dissolving the adduct in the solubilizer, diluting the resulting solution with the indicated amount of 1,2-propanediol, and adding the sodium chloride solution to the diluted solution. A control solution was also prepared for use with each test solution. The control was identical with the test solution except that it contained no adduct.

The testing involved injecting each rat with a solution of the adduct, dosage 5.0 mg per kg of body weight in one series of tests and 1.0 mg per kg of body weight in another, or with the same volume of the appropriate control, irradiating one of the two tumors while the other was shielded from light, sacrificing the animals, and examining the tumors. The injections were made via the dorsal tail vein. The irradiation of one of the tumors occurred twenty four hours after each rat was injected. The tumors were examined twelve days after treatment.

Tumor temperature and body core temperature were monitored, using thermistors, one placed into the tumor and one placed intrarectally. Tumor temperature was kept within 2° of body core temperature by directing a jet of cool air over the tumor.

The light source used for irradiation was a slide projector that had a 500 watt bulb fitted with a red filter which is available from Corning Glass Works under the designation 2418. The light was reflected 90° by a silvered mirror, and was focused onto the tumor with a secondary condensing lens. The light intensity on the tumor was monitored, using a photometer/radiometer that is available from United Detector Technology under the designation "UDT #351", and was maintained at 200 mw per cm$^2$.

Six rats were injected with each of the adduct test solutions and two were injected with the appropriate control solution.

Twelve days after the irradiation, none of the treated tumors of the rats that had been injected with 5.0 mg per kg of body weight of either adduct could be detected either by palpation or histologically, but the untreated tumors and those in the rats that had been injected with the control had continued to grow. The rats to which 1.0 mg per kg of body weight of the adducts had been administered were sacrificed by an intracardiac injection of saturated aqueous potassium chloride solution, and the control and treated tumors were harvested and desiccated to constant weight. One hundred times the dry weight of the tumors of the treated rats divided by the dry weight of the tumors of the control rats was zero for the rats treated with Adduct I and 7 for those treated with Adduct II. During the testing, the rats were under barbituate anesthesia (65 mg per kg body weight).

None of the irradiated tumors of the rats that were treated with 1.0 mg per kg of body weight of Adduct I and only fifty percent of the irradiated tumors of the rats that were treated with that dose of Adduct II could be detected palpably.

The production of Adduct I and of Adduct II by reaction between dimethyl acetylenedicarboxylate and Porphyrin I and Porphyrin II is described in examples 1 and 2, respectively. The reaction of these examples is general in the sense that it can be used to prepare Diels Alder adducts of other vinyl porphyrins which have the structure shown above. Such vinyl porphyrins are either known, or can be produced by the method described in Example 2 for the preparation of Porphyrin II from dihydroxy chlorins having the foregoing structure. The required dihydroxy chlorins are either known or can be produced by OsO$_4$ oxidation of the corresponding porphyrins, which are either known or can be produced by known reactions from the requisite dipyrrolic intermediates, e.g., dipyrromethanes and dipyrromethenes, which, in turn are either known or can be synthesized from the requisite pyrroles. The requisite pyrroles, if not available, can be synthesized by the classical Knorr Reaction and variations, and by other known reactions, and can be manipulated and transformed (see, for example, David Dolphin, *The Porphyrins*, Volume I, Structure and Synthesis, Part A, Academic Press, New Your, San Francisco and London, 1978, pages 101-163. The pyrroles have the following structure:

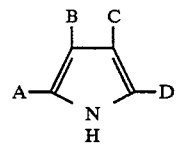

where A can be H, CH$_3$, an ester, a nitrile, a cyanovinyl or an amide group, G can be H, an ester, a nitrile, a cyanovinyl or an amide group and B and C are substituents which appear in the ultimate porphyrin, frequently lower alkyl groups, particularly methyl and ethyl.

Dipyrrolic intermediates, e.g., dipyrromethanes and dipyrromethenes, can be synthesized from pyrroles, and can be converted to porphyrins by known reactions; some porphyrins can be synthesized directly from pyrroles (see, for example, David Dolphin, supra, pages 85-100 and 163-234). Dipyrromethanes and dipyrromethenes have the following structures.

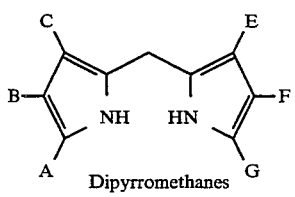

-continued

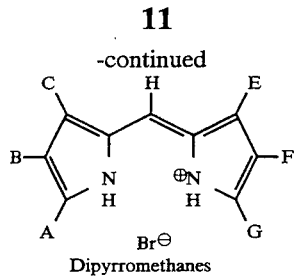

Dipyrromethanes

By way of example, "Octamethylporphyrin" can be synthesized by heating 3,4-dimethylpyrrole (foregoing structure, where A is HOOC, B and C are $CH_3$ and D is $CH_2OH$) at 160°–170° and "Octaethylporphyrin" can be synthesized by heating 3,4-diethylpyrrole, where A is HOOC, B and C are $CH_2CH_3$ and D is $CH_2OH$. Porphyrins can also be produced from dipyrromethanes by way of an aldehyde coupling reaction, a formic acid or orthoformate ester condensation, by the "dialdehyde synthesis" or by the Villsmeier pyrroketone synthesis, and from dipyrromethenes by the Fischer synthesis, or by reaction with dipyrromethanes. The porphyrins that are produced have the following structure where R is hydrogen and R1 through R4 and R5 through R8 have the same meanings as B, C, E and F in the dipyrromethane and dipyrromethene starting materials when the porphyrins are synthesized from these precursors:

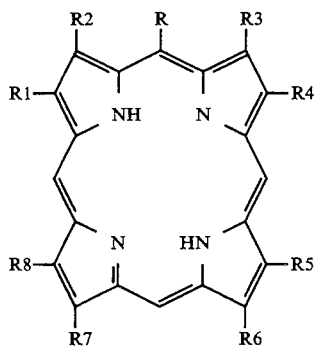

In octamethylporphyrin and octaethylporphyrin, R is hydrogen and R1 through R8 are methyl in the former and ethyl in the latter.

Example A describes the preparation of 2,3-dihydroxy-2,3,7,8,12,13,17,18-octaethylchlorin ("Chlorin II"; Chang et al, supra) from a solution of 1.168 g octaethylporphyrin and 1 mL pyridine in 250 mL dichloromethane and 1.0 g osmium tetroxide in 10 mL diethyl ether. Chlorin II has the foregoing general formula for dihydroxy chlorins where R1, R2, R3 and R4 are ethyl.

EXAMPLE A

The octaethylporphyrin/pyridine solution is mixed with the osmium tetroxide and ether, and the reaction mixture which results is stirred at room temperature of about 22° for two days. The reaction mixture is then diluted with 50 mL of methanol, and $H_2S$ is bubbled through the diluted mixture for 15 minutes. Osmium sulfide, which is precipitated by the $H_2S$, is then separated by filtration, and the solvent is evaporated from the filtrate. The residue is triturated with methanol, which dissolves the Chlorin II, leaving the octaethylporphyrin. The Chlorin II is further purified on a silica gel column using dichloromethane containing 0.5v/v methanol. The method of the first paragraph of Example 2 can then be used to synthesize Porphyrin I from Chlorin II.

It is known that metal complexes of purpurins and chlorins, particularly the tin and zinc complexes, are more effective compounds for use in photodynamic therapy than the corresponding metal-free compounds. It is contemplated that the metal complexes of the adducts according to the instant invention will also be more effective, and that they can be produced by the procedures used to prepare the purpurins and chlorins. Example B, below, illustrates the method contemplated for the preparation of such complexes.

EXAMPLE B

Production of Sn Diels Alder Adduct I

A solution is prepared by dissolving 20 mg Diels Alder Adduct I in 20 mL acetic acid and 100 mg tin chloride is added to the solution; the mixture which results is refluxed for about 24 hours until the electronic spectrum of the reaction mixture indicates that chelation is complete. The reaction mixture is then con-centrated to 7 mL and allowed to cool to room temperature of about 22°. Product which precip-itates is recovered by filtration, dissolved in a mixed solvent composed of 5 mL dichloromethane and 2 mL hexane, and recrystallized, yielding the Sn complex of Porphyrin I, which has the structure of Formula 3, supra, where R 1 through R7 are ethyl, R8 is methyl, and M is Sn.

The procedure of Example B can be used to produce metal complexes of other adducts according to the invention. Specifically, an equivalent amount of Adduct II can be substituted for the Adduct I, or zinc acetate, cobalt acetate, silver acetate, palladium acetate, or platinum acetate can be substituted for the tin chloride, or both substitutions can be made. In this manner, metal complexes of Diels Alder adducts having the structure of Formula 3 or 4 where M is Sn, Co, Ag, Pd, Pt or Zn can be produced from Diels Alder adducts having the structure of Formula 1 or2.

Other complexes can be produced by the method of Example B from salts containing cations other than acetate, and producing complexes which have the structures of Formulas 3 and 4, but where M does not represent merely a metal cation. Examples of salts that can be substituted for zinc acetate in the Example B procedure are given below, together with the identity of M in the foregoing FIGS.:

| Salt | Identity of M |
|---|---|
| $FeCl_3$ | Fe(Cl) |
| $MnCl_4$ | Mn(Cl) |
| $InCl_3$ | In(Cl) |
| $VCl_4$* | V(O) |
| $Tl(CF_3CO_2)_3$ | $Tl(OAc)(H_2O)$ |
| $SnCl_2$ | $Sn(OH)_2$ |
| $[Rh(CO)_2Cl]_2$ | $Rh(Cl)(H_2O)$ |

*Using phenol as the solvent instead of glacial acetic acid.

The procedure of Example B can also be modified by substituting phenol for glacial acetic acid and metal chelates of pentane, 2,4-dione for zinc acetate to produce complexes of any of the Diels Alder adducts. Metals that can be so reacted (as pentane, 2,4-dione chelates) and the identify of M in the complex that is produced are set forth in the following table:

| Metal | Identity of M | Metal | Identity of M |
|---|---|---|---|
| Al | Al(acac)* | Th | Th(acac)$_2$ |
| Sc | Sc(acac) | U | U(acac)$_2$ |
| Ga | Ga(acac) | La | La(acac)$_2$ |
| In | In(acac) | Ce | Ce(acac) |
| Mo | Mo(acac) | Nd | Nd(acac) |
| Ti | Ti(acac)$_2$ | Sm | Sm(acac) |
| Zr | Zr(acac)$_2$ | Gd | Gd(acac) |
| Hf | Hf(acac)$_2$ | Tb | Tb(acac) |
| Eu | Eu(acac) | Dy | Dy(acac) |
| Pr | Pr(acac) | Ho | Ho(acac) |
| Yb | Yb(acac) | Er | Er(acac) |
| Y | Y(acac) | Tm | Tm(acac) |
| Lu | Lu(acac) | | |

*The pentane, 2,4-dione portion of a chelate thereof with a metal.

Complexes of the Diels Alder adducts can also be produced by the procedure of Example B, substituting dimethylformamide for glacial acetic acid and CrCl$_2$ for zinc acetate. Metal complex formation occurs at higher temperatures when dimethylformamide is used, because of its higher boiling temperature. M in the complexes is Cr(OH).

Similarly, complexes of the Diels Alder adducts can be produced by the procedure of Example B, substituting pyridine for glacial acetic acid and PbCl$_2$ for zinc acetate. M in the complexes is Pb.

Example C, below, describes the production of a Diels Alder adduct from 500 mg Protoporphyrin IX Dimethyl ester dissolved in 50 mL dry toluene and 0.5 mL diethylacetylenedicarboxylate (see Pangka et al., *J. Org. Chem*, 1986, 51, 1094-1100).

EXAMPLE C

A reaction mixture composed of the diethyl acetylenedicarboxylate and the Protoporphyrin IX Dimethyl ester solution is refluxed in the dark at room temperature of about 22° for six days. The solvent is then removed in vacuo and the residue is chromatographed on SiO$_2$ with dichloromethane containing 2v/v diethyl ether. Two isomers, "Adduct V" and "Adduct VI", are recovered. The two adducts have the structures shown below, where R is ethyl:

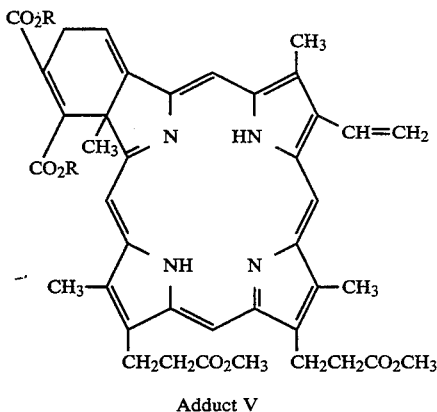

Adduct V

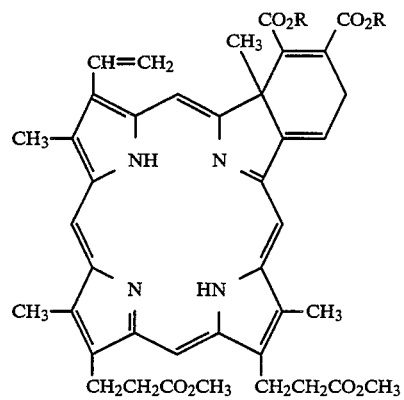

Adduct VI

The procedure of Example 3 can be used to cause a chemical shift of Adduct V to Adduct VII and of Adduct VI to Adduct VIII, compounds having the structures shown below, where R is ethyl:

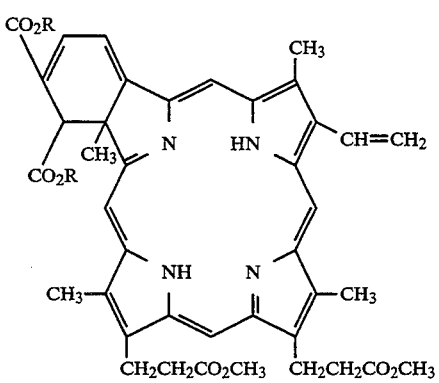

Adduct VII

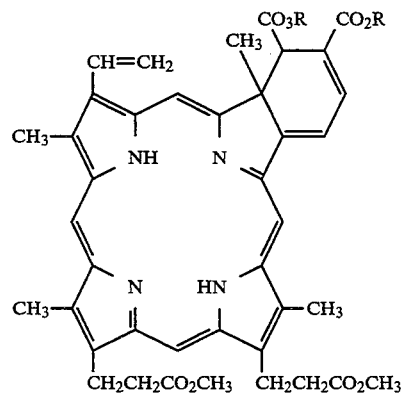

Adduct VIII

Adduct VII and Adduct VIII can be selectively reduced by treatment with hydrogen in the presence of palladium on charcoal (see Levy et al., supra), to produce Adduct IX and Adduct X, which have the following structures, where R is ethyl:

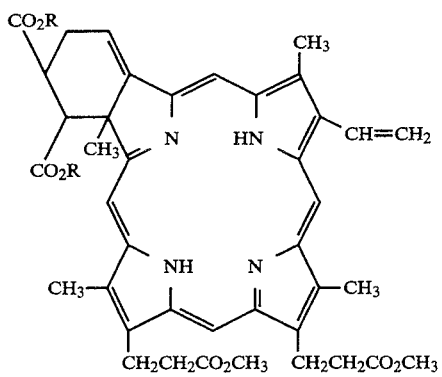

Adduct IX

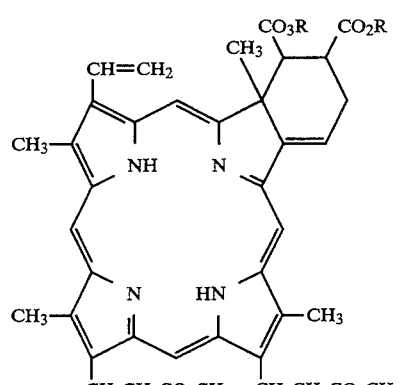

Adduct X

Metal complexes of Adducts V and VI can be produced by the procedures of Example B and the modifications thereof discussed above, producing Complex V and Complex VI, which have the following structures, where R is ethyl and M is Ag, Al, Ce, Co, Cr, Dy, Er, Eu, Ga, Gd, Hf, Ho, In, La, Lu, Mn, Mo, Nd, Pb, Pd, Pr, Pt, Rh, Sb, Sc, Sm, Sn, Tb, Tc-99m, Th, Ti, Tl, Tm, U, V, Y, Yb, Zn or Zr:

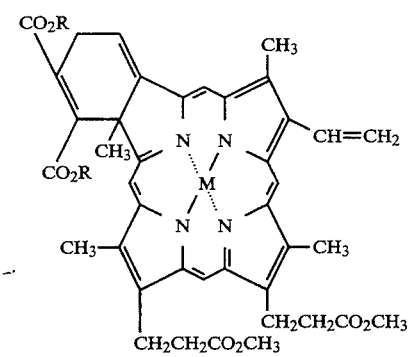

Complex V

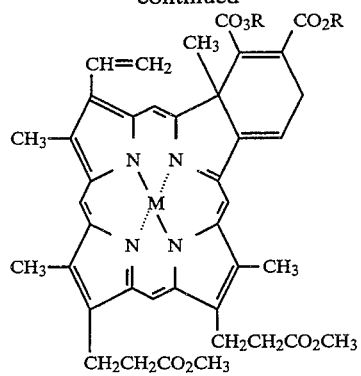

Complex VI

Similarly, metal complexes of Adducts VII and VIII can be produced by the procedures of Example B and the modifications thereof discussed above, producing Complex VII and Complex VIII, which have the following structures where R is ethyl and M is Ag, Al, Ce, Co, Cr, Dy, Er, Eu, Ga, Gd, Hf, Ho, In, La, Lu, Mn, Mo, Nd, Pb, Pd, Pr, Pt, Rh, Sb, Sc, Sm, Sn, Tb, Tc-99m, Th, Ti, Tl, Tm, U, V, Y, Yb, Zn or Zr:

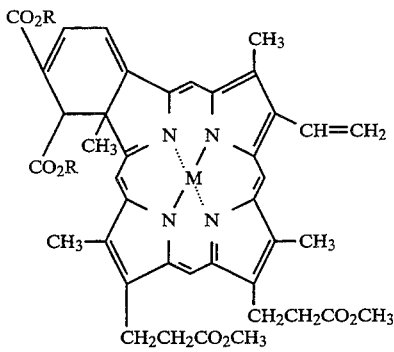

Complex VII

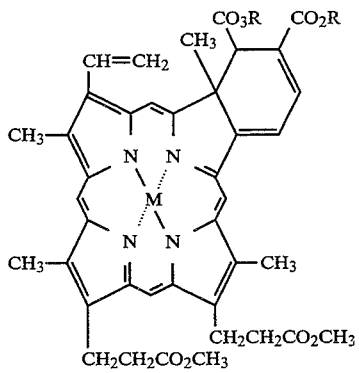

Complex VIII

Finally, metal complexes of Adducts IX and X can be produced by the procedures of Example B and the modifications thereof discussed above, producing Complex IX and Complex X, which have the following structures where R is ethyl and M is Ag, Al, Ce, Co, Cr, Dy, Er, Eu, Ga, Gd, Hf, Ho, In, La, Lu, Mn, Mo, Nd, Pb, Pd, Pr, Pt, Rh, Sb, Sc, Sm, Sn, Tb, Tc-99m, Th, Ti, Tl, Tm, U, V, Y, Yb, Zn or Zr:

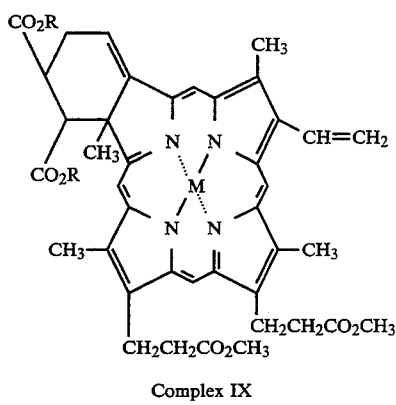

Complex IX

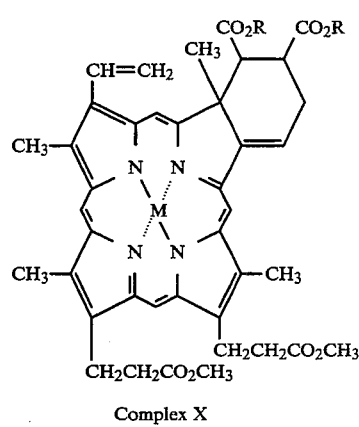

Complex X

Where any of R1 through R8 of any of the foregoing adducts or adduct metal complexes has a free CO$_2$H group, that moiety can be reacted with an amino acid moiety, which can be a monoclonal antibody, to form an amide. Example D is illustrative of such reactions:

EXAMPLE D

A Diels Alder adduct coupled to a monoclonal antibody is produced from (1) 20 mg Diels Alder Adduct metal complex produced as described above where one of R1 through R7 is CO$_2$H, CH$_2$CO$_2$H or CH$_2$CH$_2$CO$_2$H dissolved in 1.25 ml water and 0.8 ml N,N-dimethyl formamide, (2) 20 mg 1-ethyl-3-(3-dimethylaminopropyl)carbodiimide. HCl dissolved in 0.6 ml water and (3) 15 mg monoclonal antibody dissolved in 5 ml distilled water. The Adduct solution is added to the carbodiimide hydrochloride solution, and the combined solution is mixed with the monoclonal antibody solution. After 30 minutes, the reaction is quenched by adding 0.05 ml monoethanol amine, and the conjugated material, i.e., the amide of the monoclonal antibody and the Adduct, is dialyzed exhaustively at 4° against 0.001N phosphate buffered saline, pH 7.4.

The procedure of Example D is generally applicable to couple proteins and amino acids which, as in the example, can be monoclonal antibodies to Diels Alder Adducts and metal complexes thereof having the structures of formulas 1 through 8 where one of R1 through R8 is a CO$_2$H or the like group.

In the procedures described above, Diels Alder adducts were produced by reactions between a vinyl compound and either dimethyl acetylenedicarboxylate or diethyl acetylenedicarboxylate. Other acetylenedicarboxylates, e.g., ones where the two alkoxy groups can be the same or different, and each has the formula R8O- where R8 is an alkyl group other than t-butyl having from one to four carbon atoms, can be substituted, so that the two R8 groups in the foregoing formulas can be the same or different, and each can be an alkyl group other than t-butyl having from one to four carbon atoms.

It will be appreciated that various changes and modifications are possible from the specific details of the invention as described above without departing from the spirit and scope thereof as defined in the following claims.

We claim:

1. A Diels Alder adduct having the structure of Formula 1 or of Formula 2, or a metal complex of a Diels Alder adduct having the structure of Formula 3 or of Formula 4, below:

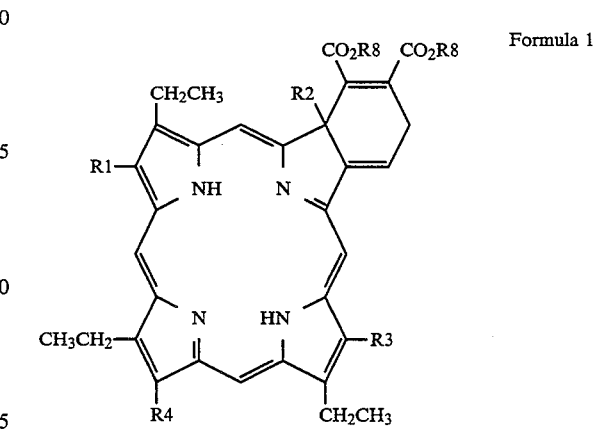

Formula 1

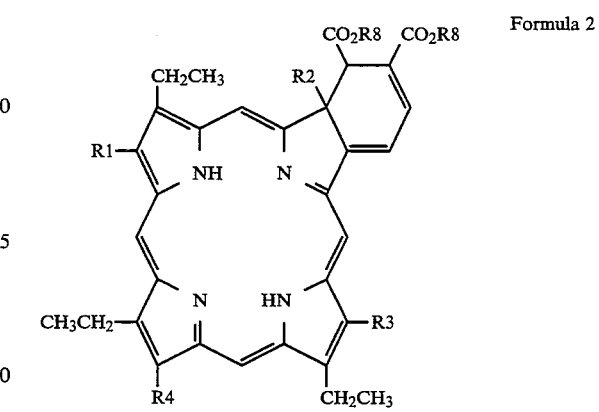

Formula 2

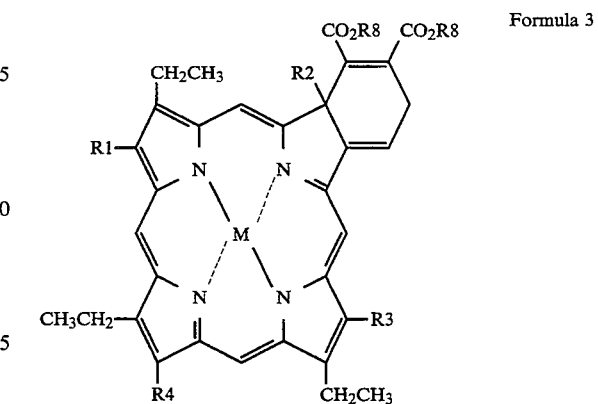

Formula 3

-continued

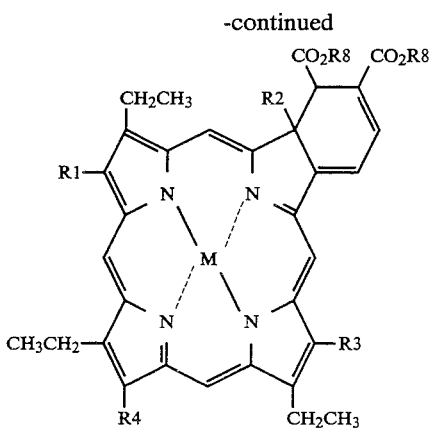

Formula 4 where R1, R2, R3 and R4 can be the same or different, and each is methyl or ethyl, R8 is an alkyl group other than t-butyl having from one to four carbon atoms and M is Ag, Al, Ce, Co, Cr, Dy, Er, Eu, Ga, Gd, Hf, Ho, In, La, Lu, Mn, Mo, Nd, Pb, Pd, Pr, Pt, Rh, Sb, Sc, Sm, Sn, Tb, $^{99m}$Tc, Th, Ti, Tl, Tm, U, V, Y, Yb, Zn or Zr.

2. A metal complex of a Diels Alder adduct as claimed in claim 1 having the structure of Formula 3 or Formula 4.

3. A metal complex of a Diels Alder adduct as claimed in claim 2 wherein M is Sn or Zn.

* * * * *